(12) United States Patent
Qureshi et al.

(10) Patent No.: US 9,107,697 B2
(45) Date of Patent: Aug. 18, 2015

(54) SYSTEM AND METHOD FOR SELECTING FOLLICULAR UNITS FOR HARVESTING

(75) Inventors: Shehrzad A. Qureshi, Palo Alto, CA (US); Hongze Liu, Fremont, CA (US)

(73) Assignee: Restoration Robotics, Inc., San Jose, CA (US)

( * ) Notice: Subject to any disclaimer, the term of this patent is extended or adjusted under 35 U.S.C. 154(b) by 1276 days.

(21) Appl. No.: 12/133,159

(22) Filed: Jun. 4, 2008

(65) Prior Publication Data

US 2009/0306680 A1     Dec. 10, 2009

(51) Int. Cl.
*A61B 17/32*     (2006.01)
*A61B 19/00*     (2006.01)
*A61B 17/00*     (2006.01)
*A61F 2/10*      (2006.01)

(52) U.S. Cl.
CPC ............. *A61B 19/5212* (2013.01); *A61B 19/22* (2013.01); *A61B 19/50* (2013.01); *A61B 2017/00752* (2013.01); *A61B 2019/5227* (2013.01); *A61F 2/10* (2013.01)

(58) Field of Classification Search
CPC ...................... A61B 17/32053; A61B 19/2203; A61B 2018/00476; A61B 2017/00752
USPC ...................... 606/133, 187; 33/512; 700/245
See application file for complete search history.

(56) References Cited

U.S. PATENT DOCUMENTS

| | | | |
|---|---|---|---|
| 4,063,822 A | 12/1977 | deJong et al. | |
| 4,807,163 A | 2/1989 | Gibbons | |
| 5,865,744 A | 2/1999 | Lemelson | |
| 6,470,236 B2 * | 10/2002 | Ohtsuki | 700/247 |
| 6,477,394 B2 | 11/2002 | Rice et al. | |
| 6,504,603 B1 | 1/2003 | Schouenborg | |
| 6,547,782 B1 | 4/2003 | Taylor | |
| 6,572,625 B1 | 6/2003 | Rassman | |
| 6,585,746 B2 | 7/2003 | Gildenberg | |
| 6,949,115 B2 | 9/2005 | Mascio | |
| 7,014,336 B1 | 3/2006 | Ducharme et al. | |

(Continued)

FOREIGN PATENT DOCUMENTS

| | | |
|---|---|---|
| CN | 101128156 | 2/2008 |
| WO | 00/64379 | 11/2000 |

(Continued)

OTHER PUBLICATIONS

PCT Notification of Transmittal of the International Search Report and the Written Opinion of the International Searching Authority. International Application No. PCT/US2009/045500. Forms PCT/ISA/220, 210 & 237. (15 Pages).

(Continued)

*Primary Examiner* — Thomas McEvoy
*Assistant Examiner* — Julie A Szpira
(74) *Attorney, Agent, or Firm* — Lena I. Vinitskaya; Sharon Upham (57) ABSTRACT

A system and method for selecting follicular units for hair harvesting using imaging and processing techniques are provided. The method of selecting an order of harvesting follicular units is based on a combination of one or more policies and filters that are generally designed to improve a speed, quality and efficacy of the harvesting process. The method of the present invention may be implemented with various hair harvesting and transplantation systems, including manual, partially automated and fully automated systems.

25 Claims, 8 Drawing Sheets

(56) References Cited

U.S. PATENT DOCUMENTS

| | | | |
|---|---|---|---|
| 7,130,717 | B2 | 10/2006 | Gildenberg |
| 7,206,627 | B2 | 4/2007 | Abovitz et al. |
| 7,239,909 | B2 | 7/2007 | Zeman |
| 7,290,896 | B2 | 11/2007 | Dallas et al. |
| 7,477,782 | B2 * | 1/2009 | Qureshi et al. ............ 382/171 |
| 7,517,107 | B2 | 4/2009 | Dallas et al. |
| 7,545,487 | B2 | 6/2009 | Kok et al. |
| RE42,381 | E | 5/2011 | Gildenberg |
| 2002/0103500 | A1 * | 8/2002 | Gildenberg .............. 606/187 |
| 2004/0034282 | A1 | 2/2004 | Quaid |
| 2004/0204700 | A1 * | 10/2004 | Weaver et al. ............ 604/500 |
| 2006/0089555 | A1 | 4/2006 | Gummer et al. |
| 2007/0043341 | A1 * | 2/2007 | Anderson et al. ............ 606/12 |
| 2007/0078466 | A1 * | 4/2007 | Bodduluri et al. .......... 606/133 |
| 2008/0154247 | A1 | 6/2008 | Dallarosa et al. |
| 2008/0216334 | A1 | 9/2008 | Pak et al. |
| 2009/0237920 | A1 | 9/2009 | Dallas et al. |
| 2009/0245601 | A1 | 10/2009 | Cohen et al. |
| 2011/0082369 | A1 | 4/2011 | Mohr et al. |
| 2011/0160589 | A1 | 6/2011 | Fu et al. |

FOREIGN PATENT DOCUMENTS

| | | |
|---|---|---|
| WO | 2006/071728 | 7/2006 |
| WO | WO2008024954 | 2/2008 |
| WO | WO2008024955 | 2/2008 |

OTHER PUBLICATIONS

Examiner's First Report in connection with commonly assigned Korean Patent Application No. 2010-7026383, and translation thereof. Applicant: Restoration Robotics, Inc., dated May 9, 2012 (6 pages).

Mohammed Alhaddab, MD; Thomas Kohn, MD; and Mark Sidloi, BSc. Effect of Graft Size, Angle, and Intergraft Distance on Dense Packing in Hair Transplant. Dermatol Surg 2005; 31: pp. 650-654. Published by BC Decker Inc.

Rolf Hoffmann and Dominique van Neste. "Recent Findings with Computerized Methods for Scalp Hair Growth Measurements". J Investig Deramtoal Symp Proc 10:285-288, 2005.

Robert M. Bernstein, MD, and William R. Rassman, MD. "The Logic of Follicular Unit Transplantation". Dermatologic Clinics, vol. 17, No. 2, Apr. 1999.

English Translation of Office Action mailed Nov. 27, 2012, in relation to commonly assigned Korean Patent Application No. 2010-7026383, 4 pages.

English Translation of Office Action mailed Apr. 23, 2013, in relation to commonly assigned Chinese Patent Application No. 200980117701.0, (6 pages).

Translation of Examiner's First Office Action in connection with commonly assigned Chinese Patent Application No. 200980117701.0, Applicant: Restoration Robotics, Inc., dated Aug. 2, 2012 (6 pages).

Translation of Examiner's Office Action in connection with commonly assigned Japanese Patent Application No. 2011-512533; Applicant: Restoration Robotics, Inc., dated Sep. 18, 2012 (3 pages).

Office Action mailed Feb. 10, 2014 in connection with commonly assigned European Patent Application No. 09759083.0. Applicant: Restoration Robotics, Inc., (5 pages).

English Translation of Office Action mailed Oct. 29, 2013 in connection with commonly assigned Chinese Patent Application No. 200980117701.0. Applicant Restoration Robotics, Inc. (9 pages).

English Translation of Office Action mailed Apr. 21, 2015, in relation to commonly assigned Chinese Patent Application No. 200980117701.0, Apr. 21, 2015, 8 pages.

English Translation of Korean Office Action mailed Aug. 19, 2014, in connection with commonly assigned Korean Patent Application No. 2013-7015877, Restoration Robotics, Inc. (4 pages).

* cited by examiner

FUs to be ignored — 10, 12, 14

"selection region-of-interest"

Fig. 3 segmented FU image (a)  (b)  (c)  (d)

↓ thinning

FU skeleton cycle

Fig.5A

Blood red light

Fig.5B white light

Fig.6

Non-bloody regions of the scalp
(more texture => larger variance)

Bloody regions of the scalp
(less texture => lower variance)

Fig.7

Left                    Right

Fig. 8A

Policy: skip every N FU
N=1

Fig. 8B

Policy: skip every N FU
N=2

SYSTEM AND METHOD FOR SELECTING FOLLICULAR UNITS FOR HARVESTING

FIELD OF INVENTION

This invention relates generally to hair transplantation procedures and more particularly to a system and method for selecting follicular units for hair harvesting using imaging and processing techniques.

BACKGROUND

Hair transplantation procedures are well-known, and typically involve harvesting donor hair grafts from the donor areas, for example, side and back fringe areas of the patient's scalp or other surface containing hair, and implanting them in a bald area (recipient area). Historically, the harvested grafts were relatively large (3-5 mm), although more recently, the donor grafts may be single follicular units. In particular, "follicular units" (also referred to as FU or FUs) are naturally occurring aggregates of 1-3 (and much less commonly, 4-5) closely spaced hair follicles that are distributed randomly over the body surface, such as a scalp.

The follicular units may be classified, or "typed," based on the number of hairs in the unit and identified in shorthand as an "F1" for a single hair follicular unit, an "F2" for a two hair follicular unit and so on for follicular units with 3-5 hairs. It is desirable to identify follicular units based on the number of hairs in the follicular unit. For one, it is preferable to transplant certain classes of follicular units into specific regions of the scalp. For example, single hair follicular units (F1s) are commonly implanted along the hairline that frames the face. Follicular units with more than one hair (F2s, F3s, etc.) are commonly implanted in the mid-scalp and crown. This arrangement of follicular unit distribution is thought to produce a more natural appearing aesthetic result. Still, it may be desirable to utilize a variety of classes (also referred to as "types") of follicular units to provide the desired attributes for the appearance of the transplanted hair. Such attributes can include the density of hair, the direction or orientation of hair, the particular mix of types of follicular units, and/or the appearance of randomness, among other possible attributes.

Various procedures for hair transplantation have been previously disclosed, including both manual and mechanized to certain degrees of automation. In one well-known manual process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so. In another manual process, a hand-held punch or cannula is used to extract follicular units from a body surface one at a time for subsequent implantation in another location. This technique is known as FUE (follicular unit extraction) technique.

U.S. Pat. No. 6,585,746 discloses an automated hair transplantation system utilizing a robot, including a robotic arm and a hair follicle introducer associated with the robotic arm. In utilizing any of the manual or automated systems and methods for hair transplantation, it is desirable to improve the speed and efficiency of the procedure. Regardless of the system used, certain time is often lost due to the need to select the next follicular unit to be harvested and to move the hair harvesting tool from the position of previously harvested follicular unit to the location of the next selected follicular unit. Therefore, there is a need for a system and method for automated selection mechanism for choosing follicular units for harvesting and improving efficiency of the process as a whole.

SUMMARY

In accordance with a general aspect of the inventions disclosed herein, a system and method for selecting follicular units to be harvested using an automated system are provided. The system and method of the present invention may be utilized with systems and methods for transplantation of hair follicular units on a body surface. The system and method of the present invention is especially useful when implemented on, or integrated with, an automated system for hair transplantation.

In one aspect of the present invention, the method of selecting an order of harvesting follicular units is provided. In some embodiments, the method comprises identifying a pool of candidate follicular units for harvesting in one or more images of a surface containing follicular units, automatically sorting follicular units in the pool of candidate follicular units based on one or more policies, and automatically selecting a particular follicular unit to be harvested next. One or more policies are generally designed to improve one or all of a speed, quality, and efficacy of the hair harvesting. The selected follicular unit is one of the best available follicular units based on the at least one or more policies. There may be only one policy or a plurality of predetermined policies, each one given a certain weight so that when multiple policies are used, sorting follicular units comprises scoring them based on a weighted sum of variables comprising these multiple policies. Some exemplary policies include a follicular unit type, a distance to a harvesting tool, follicular unit orientation, an emergence angle from the body surface, simplicity of the shape of the follicular unit. Additional examples of the policies useful in the method of the present invention include skipping every Nth follicular unit in the pool of candidate follicular units where N is chosen based on a particular situation, including any future harvesting planning.

In certain embodiments, the method of the present invention provides for automatic filtering of the follicular units from the pool of candidate follicular units based on a predetermined criterion. In yet further embodiments, automatic selection of the particular follicular unit to be harvested next is based on a combination of a plurality of filters and policies. Each of the filters and policies can be turned on or off, depending on the clinical situation. Some examples of filtering according to the present invention includes discarding follicular units that are located within a certain minimum distance to another follicular unit, or to an edge of the field of view of the image, or to a location containing blood. Further examples may include filtering by discarding follicular units that are less than a predetermined width, or possess a complex shape, or do not meet a predetermined desired criterion based on the number of hairs emanating from a follicular unit, or have not consistently appeared in a predetermined preceding time interval. Filtering according to the present invention can be done either "negatively" by excluding certain hairs that fall within or outside a predetermined parameter or criterion, or "positively" by including only those hairs that either fall within or outside a predetermined parameter or criterion.

The method of the present invention may be used in a manual procedure conducted by a physician with a hand-held device, or it may be used with some automated system, it is especially useful with the robotic hair harvesting systems. When used with the robotic hair harvesting system, one exemplary method of the present invention may comprise identifying a pool of candidate follicular units for harvesting in one or more images of a surface containing follicular units, automatically sorting follicular units in the pool of candidate follicular units based on one or more policies designed to improve one or more of speed, quality and efficacy of the hair harvesting, automatically selecting a particular follicular unit to be harvested next, wherein a selected follicular unit is one of the best available follicular units based on the at least one or more policies; and maneuvering a robotic arm of the robotic system to place a hair harvesting tool operatively connected to the robotic arm next to the selected FU to be harvested.

According to another aspect of the present invention, a system for selecting follicular units using an automated system is provided. The system comprises an image acquisition device and an image processor, wherein the image processor may be configured for identifying a pool of candidate follicular units for harvesting in one or more images obtained from the image acquisition device; automatically sorting follicular units in the pool of candidate follicular units based on one or more policies (such policies may be designed to improve speed and/or quality, and/or efficacy of the hair harvesting); and automatically selecting a particular follicular unit to be harvested next, wherein a selected follicular unit is one of the best available follicular units based on the at least one or more policies.

One example of the image acquisition device is one or more cameras, such as any commercially available cameras. Instead of a camera, it could be a video recording device (such as a camcorder) or any other image acquisition device. The image processor may comprise any device programmed and configured to perform the method of selecting follicular units according to the present invention. One non-limiting example of a suitable image processor is any type of personal computer ("PC"). One exemplary image processor of the present invention for selecting follicular units is configured for identifying a pool of candidate follicular units for harvesting in one or more images obtained from an image acquisition device; automatically sorting follicular units in the pool of candidate follicular units based on one or more policies; and automatically selecting a particular follicular unit to be harvested next, wherein a selected follicular unit is one of the best available follicular units based on the at least one or more policies.

The image processor for selecting follicular units could be used in conjunction with various manual and automated (including robotic) hair transplantation and treatment systems and devices, including but not limited to systems for hair harvesting, or hair transplantation, or hair classification, or hair treatment planning systems.

According to still another aspect of the present invention, an article of manufacture is provided that comprises a machine-accessible medium including data that, when accessed by a machine, cause the machine to perform operations, such as identifying a pool of candidate follicular units for harvesting in one or more images obtained from an image acquisition device; automatically sorting follicular units in the pool of candidate follicular units based on one or more policies, such as those designed to improve speed, quality, and/or efficacy of the hair harvesting; and automatically selecting a particular follicular unit to be harvested next, wherein a selected follicular unit is one of the best available follicular units based on the at least one or more policies.

Accordingly, a system and method for selecting follicular units are provided. Other and further embodiments, objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which.

DETAILED DESCRIPTION OF THE ILLUSTRATED EMBODIMENTS

In the following Detailed Description, reference is made to the accompanying drawings that show by way of illustration some exemplary embodiments in which the invention may be practiced. In this regard, directional terminology, such as "top," "bottom," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system, and are especially beneficial with the robotically-assisted systems and procedures. The adverb "automatically" when referring to use of a particular component of a system or a particular step in a process means that such step is accomplished autonomously, i.e., without real-time manual assistance.

The term "tool" or "harvesting tool" as used herein refers to any number of tools or end effectors that are capable of removing or harvesting follicular units ("FUs") from a body surface. It is understood that the body surface could be any area of the body having hair, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The terms "coupled," or "attached," or "mounted" as used herein, may mean directly or indirectly coupled, attached, or mounted through one or more intervening components.

Embodiments of the methods of the present invention may be implemented using computer software. Various programming languages and operating systems may be used to implement the present invention.

Manual hair harvesting procedures where individual follicular units are harvested using FUE technique are time consuming procedures as each individual FU is being separately harvested from the body surface. Even with the partially automated or fully automated harvesting procedures and systems, a certain time is required to make and execute various selection decisions when choosing the next FU to be harvested. The automatic selection system of the present invention is designed to increase the efficacy of the harvesting process in both manual and automated procedures, and it is especially useful, for example, in a robotic hair harvesting procedure.

Robotic hair transplantation systems and methods are described in the commonly assigned Published Patent Application US 2007/0078466 ("the Bodduluri et al. publication") which is incorporated herein by reference in its entirety. The above-mentioned application explains that the hair harvesting tool is carried on a moveable (e.g. robotic) arm and the arm is repositioned each time after follicular unit is harvested to move and align the harvesting tool with the next follicular unit to be harvested under the guidance of the imaging system. Of course, each such movement, repositioning and realignment of the moveable arm (and, therefore, the tool carried by the arm) takes times and increases the duration of the procedure as a whole. Therefore, it is highly desirable to design an efficient plan where movement and reorientation of the arm (and the tool) is minimized from one FU to another.

When harvesting hair follicles, it is desirable to align the harvesting tool with the follicular unit to be harvested. The better is the needle to follicular unit alignment, the lower is the chance of hair transaction, therefore, it may be ideal to aim for near perfect alignment between the needle and follicular unit (for example, having their respective axes parallel or at a certain desired small angle to each other). To achieve this goal, one potential policy or strategy to employ would be to pick an FU amongst a population of candidate FUs whose orientation most closely matches that of the previously harvested FU. In this manner the total movement of the robotic arm carrying the tool is minimized, which in turn minimizes the time to align, and consequently reduces the overall treatment time. Yet another alternative possibility is to simply pick the FU closest to the current location of harvesting tool, such as a needle or cannula.

In addition to pure consideration of the distance of the movement of the harvesting tool, the throughput of the overall procedure also depends on various additional factors that could be taken into consideration, such as the efficacy of the imaging and quality of the harvested follicular units. For example, potential FUs candidates for harvesting may be very close to a recent harvest site which, generally, would suggest them as very good candidates from the distance/timing point of view. However, if there was an excessive bleeding around any of them due to the prior immediate harvesting in that area, it is consequently preferred to avoid this region because excessive amounts of blood run a higher risk of confusing the associated image processing. Similarly, while being in close favorable position to the previous harvesting site, the potential candidate follicular unit may be too close to another follicular unit such that by harvesting the candidate FU, the neighboring FU may be damaged or transected. Moreover, due to clinical concerns, such as potential additional harvesting procedures in the future or a need to reduce scarring, the closest follicular unit may not be desirable. Therefore, such a candidate FU may have to be avoided (filtered out) despite its basic favorable proximity to the previous harvesting site.

It is noted here that due to patient variability and numerous factors affecting the procedure and potential future anticipated follow-up procedures, the best strategy may involve a combination of different "filters" and "policies". For example, the method may include one or several main policies for sorting available follicular units for harvesting, and in addition, the population of candidate FUs may be also filtered according to one or several criteria. For example, those FUs in close proximity to bloody portions of the scalp may be filtered. Then the remaining FUs may be sorted via a policy of preferring FUs close to the current needle position, and whose orientation matches the FU that was just harvested. As will be understood by those skilled in the art, a policy may be set up and/or described as a filter. However, regardless of how it is called, it shall fall within the scope of the present invention and shall be considered a policy if it is directed to selecting follicular unit(s) for harvesting. It should be noted that the system is runtime-configurable, meaning that each of the filters and policies can be turned on or off, depending on the clinical situation.

Figure 1:
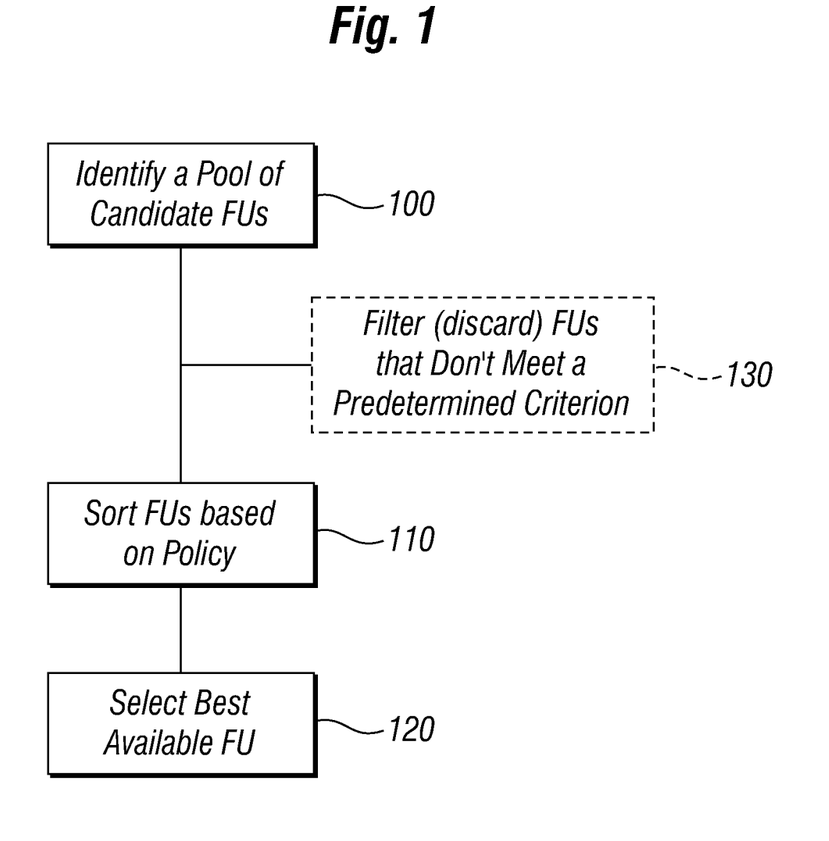
FIG. 1 is a block diagram of the exemplary automatic follicular unit selection process of the present invention.

FIG. 1 is a block diagram of the exemplary automatic follicular unit selection process of the present invention. First, at step 100 a pool of candidate follicular units for harvesting is identified in one or more images of a surface containing follicular units. At step 110, follicular units from the pool are automatically sorted according to one or several policies. There may be only one policy, alternatively, there may be several different predetermined policies, some designed to improve speed of the procedure, some may be directed to efficacy, reduced hair transaction, and various additional goals, as described in more detail below. At step 120, a particular follicular unit to be harvested next is automatically selected as one of the best available follicular units according to the above policies. Block 130 is shown by broken line to indicate that it is an optional step to the method in its generic form. At step 130, an automatic filtering of follicular units based on some criterion is performed, for example, follicular units that do not meet one or more criteria are automatically filtered from the pool of candidate FUs. It should be noted that the filtering can be done either "negatively" by excluding certain hairs that fall, for example, within or outside a predetermined parameter or criterion, or "positively" by including only those hairs that either fall within or outside a predetermined parameter or criterion. Either of these approaches is contemplated by the present invention, therefore, any reference in the description and/or in the claims to a filtering by discarding follicular units according to a certain criterion automatically includes filtering by keeping follicular units outside of or opposite to that certain criterion. Many various filters could be used dependent on specifics of each situation as described in more detail below.

Figure 2:
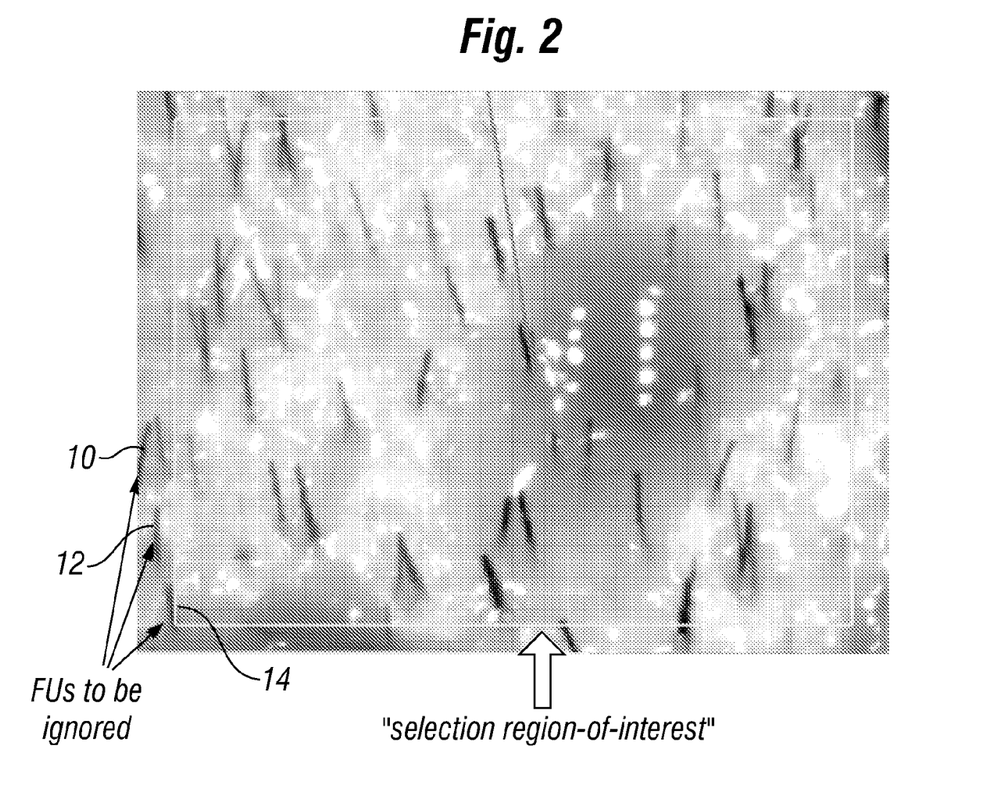
FIG. 2 is a print of a digital image of one exemplary filtering criterion according to the method of the present invention.

With reference to FIG. 2, a print of a digital image shows an example of selecting a region-of-interest by filtering FUs that could leave the field of view (FOV). More specifically, as seen in FIG. 2, FUs 10, 12 and 14 which are too close to the edge of the FOV are ignored/filtered, since there is a good chance that these FUs might be lost due to patient movement due to leaving the FOV. In FIG. 2, note that a selection of the region-of-interest (ROI) can be dialed up or down, depending on the amount of patient movement. Typical values for this "selection ROI" are 75% of the total area of the image frame.

Another example of the alternative filtering criterion is follicular units that have not been registered with the image processor for a minimum amount of time, for example, in a predetermined preceding time interval. When blood from a nearby wound (created by preceding harvesting of another follicular unit) is seeping into the region from which the next follicular unit is selected, it often may corrupt at least portions or certain frames of the image processing. As a result, a particular FU may be seen in one frame and then not being seen in a subsequent frame. Follicular units that are continually registered by the image processor are considered "stable" and, therefore, provide higher confidence for reliable harvesting. Therefore, it may be desirable in some situations to filter out FUs that are "not stable" or, putting it another way, filter in those FUs that are "stable" as explained above.

Yet another useful filtering criterion is a particular type of follicular units that are desired for harvesting or, to the contrary, should be avoided. For example, follicular units F1 and F2 are typically highly desirable, so the filter could be set up to ignore F3s and above ("don't care" type of filter), or it could be set up to select only F1s and F2s. Similarly, a filter that precludes hairs not of a minimum caliber, or width (typically at least 75 um) is useful for avoiding miniaturized or wispy FUs. "Wispy" hairs are characterized by a smaller than normal caliber, and are problematic when it comes to transections. Moreover, wispy hairs tend to have more image processing problems due to a greater propensity of getting lost amidst a constantly varying and busy scene.

Several additional examples of the filtering criteria are listed below. In many cases, measuring which way the FU is pointing relative to the scalp surface may be a key factor in orientation of the harvesting tool relative to the FU. There are certain cases where this measurement may be noisy (for example, due to blood or imaging noise because of light-colored or grayish hairs). As a result, it may be desirable to filter FUs that do not meet specified orientation stability criteria. In other cases, the filtering criterion is whether one FU is too close to another FU. "Too close" may be a function of the harvest needle diameter. If two FUs are close enough together, then extraction of one will very likely lead to transection of the neighbor. This is a situation best avoided, and therefore, the corresponding filter could be implemented.

Figure 3:
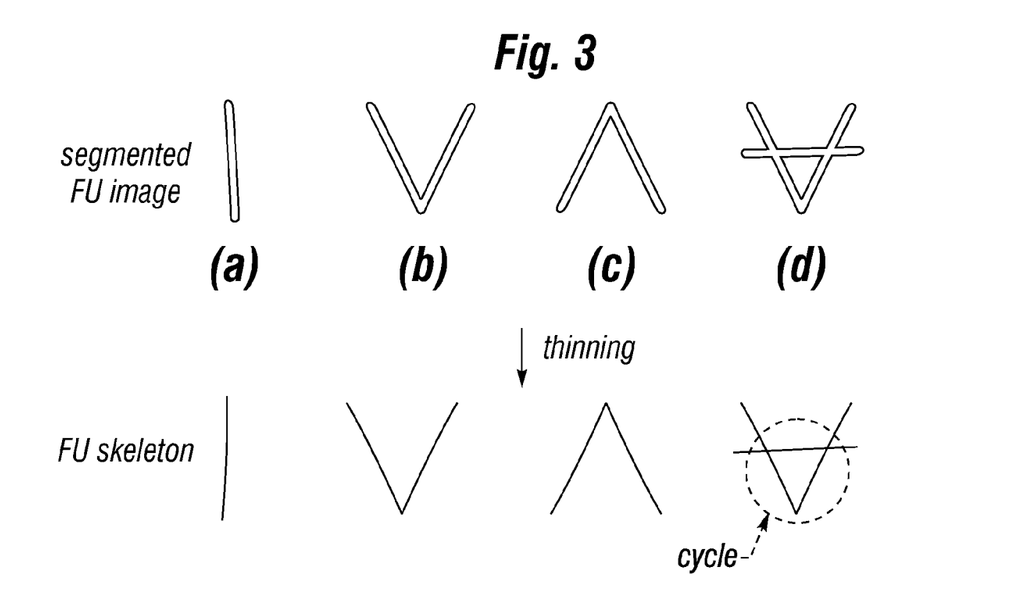
FIG. 3 is a schematic representation of another exemplary filtering criterion according to the method of the present invention.

Some FUs possess a complex shape, which is indicative of an FU that may cause problems during alignment with the harvesting tool. Better alignment results in more accurate FU extractions and reduction of the FU transaction rates. In light of that, one may prefer "simple" F1s or F2s over FUs having complex shape and configuration. "Simple" refers to FUs that have simple shapes. For example, the "V" shape is considered to be fairly simple amongst F2 shapes. FIG. 3 shows four representative segmented FUs (in the upper row of the figure), and their corresponding "skeletons" (in the lower row). Generating a skeleton or "skeletonization" is a process for reducing foreground regions in segmented image to a skeletal remnant that largely preserves the extent and connectivity of the original region of the image while discarding most of the original foreground pixels. This reduction of the foreground region occurs by peeling off a pattern of as many pixels as possible without affecting the general shape of the object being imaged. There are different ways of computing the skeleton of a segmented image. One exemplary approach is the thinning approach, where one successively erodes away pixels from the boundary while preserving the end points of line segments until no more thinning is possible (at which point what is left is the skeleton). As seen in FIG. 3, segmented image (d) is a F2 whose skeleton contains a "cycle" due to an uncut hair occluding a portion of the F2. Cycles and other noisy skeletal shapes derived from the segmented FU images make it more difficult to discern the major axis of the FU, which interferes with alignment of the tool to the FU. Therefore, one may want to exclude FUs whose morphology is not one of a straight line or curve, a V, or upside-down V. In one exemplary embodiment of the present invention, it is achieved by first pruning the skeleton (removal of "twigs") and then classifying FUs into "simple" and "complex" bins.

Figure 4:
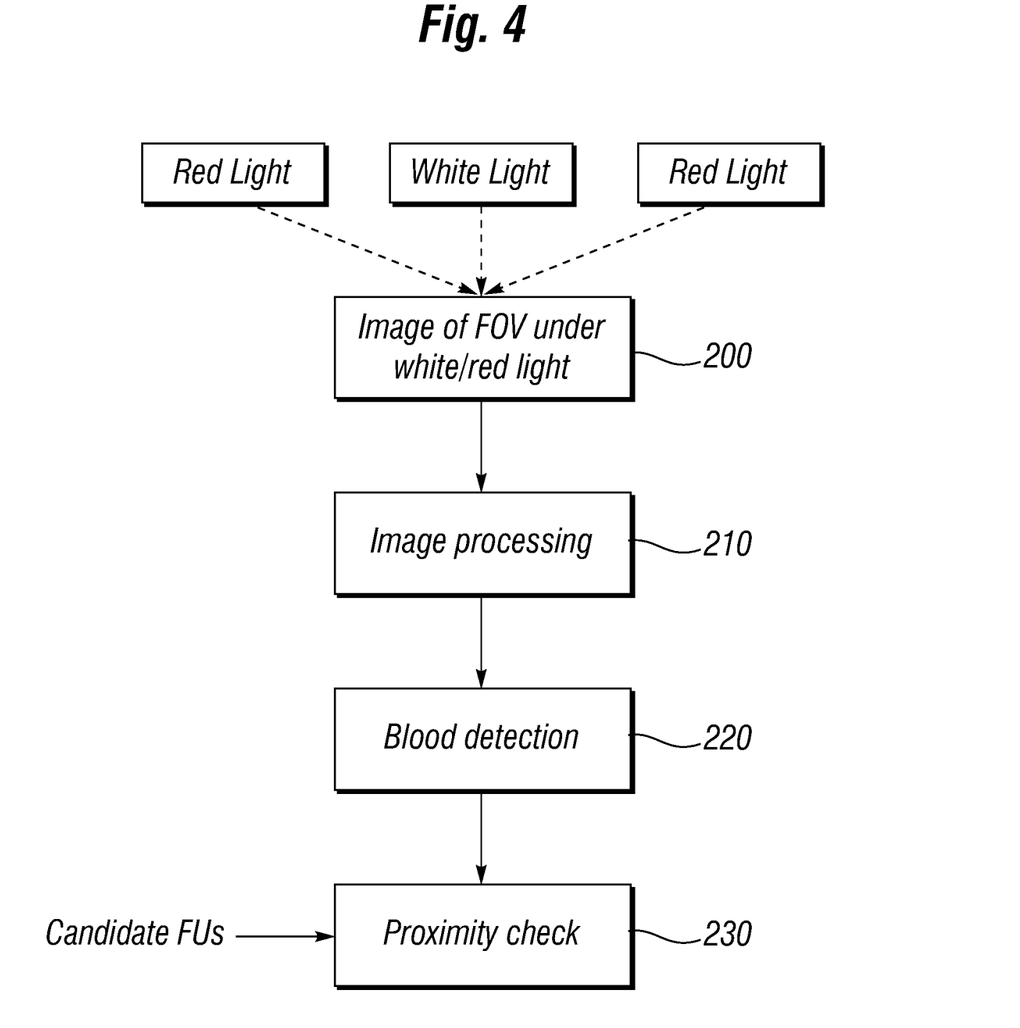
FIG. 4 is an exemplary block diagram of the blood region detection and proximity check according to yet another filtering criterion of the present invention.
Figure 5A:
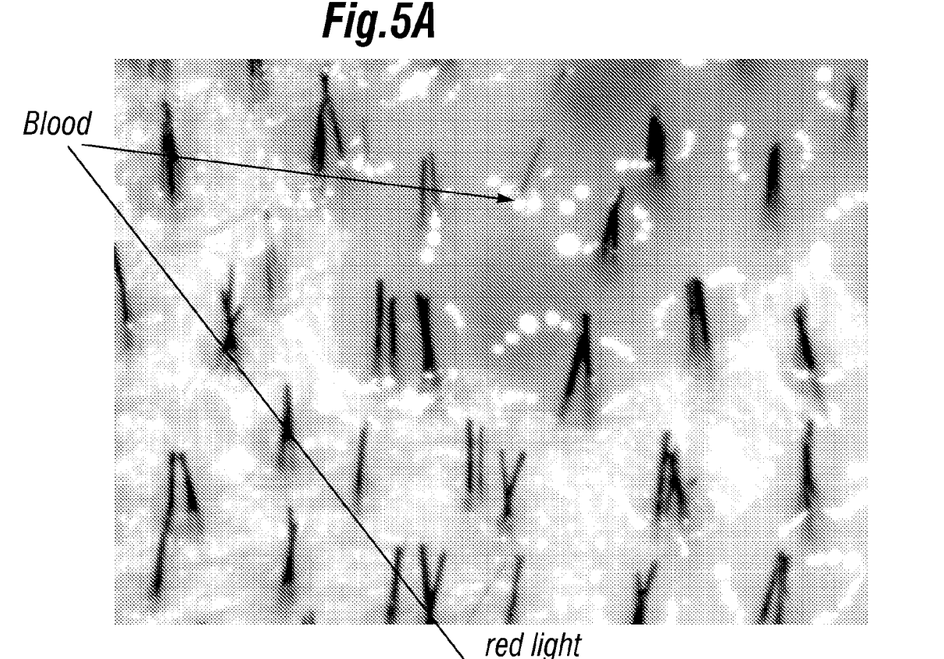
FIGS. 5A and 5B are prints of the exemplary digital images of the blood region (of FIG. 4) under red/white light.
Figure 5B:
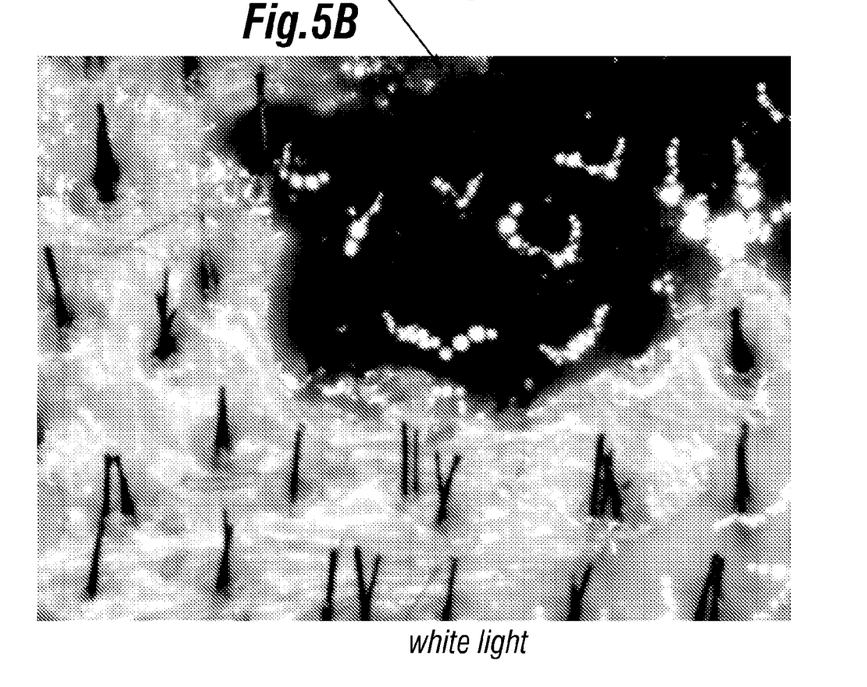

Further filtering criterion that is contemplated with the selection method of the present invention are FUs that are too close, or even lie within, bloodied or bruised regions of the body surface, such as a scalp. This typically means the FUs in question are too close to a recent harvest site. In order to minimize transection rates, it is desirable to maintain a given density of harvest sites, and this density is closely related to the harvesting punch diameter. Therefore, by identifying previously harvested sites through image processing, it is possible to spread out the FUs evenly within the donor area. Moreover, blood will tend to contaminate imaging measurements, so there are many various reasons to exclude those hairs which are too close to blood. FIG. 4 is an exemplary block diagram of the blood region detection and proximity check depicting one example of how the imaging and processing systems of the present invention ascertain which portions of the imaged scalp are bloody regions that should be avoided. During the exemplary process as shown in FIG. 4, at step 200 one or more images of the area of interest or FOV using white light are taken, which highlights blood (at the expense of hair, due to excessive glare and reflection). The motivation of this "white flash" can be noted in FIGS. 5A and 5B where the blood is much more obvious under white light than under red light. Also, one or more images of the area of interest or FOV using red light are taken to highlight follicular units, as seen in FIG. 5A. Of course, the order of taking pictures using white and red light is not important. At step 210, images taken at step 200 are processed. The images taken under the red light may be processed, for example, according to the FU counting and classification techniques described in commonly assigned co-pending published applications WO 2008/024954 and WO 2008/024955. Processing of the images taken under the white light may include, for example, various segmentation techniques and steps (as known in the art), including by way of example and not limitation fixed thresholding followed by post-processing binary erosion. At step 220, the areas containing blood are determined and, for example, a list of bloody areas may be generated. At the same time, as a result of the processing of the images containing follicular units, the list of follicular units within the same area of interest of FOV may be generated as well. At step 230, a proximity check is performed. From the pool of candidate FUs, those hairs which are found to be too close (typically within 10 pixels) in relation to a "blood region" are excluded from the selection process. Again, this filtering can be done either "negatively" by excluding those hairs that are within certain range of pixels from the bloody region or "positively" by including only those hairs that are outside the above range. Only those FUs that pass the proximity check will be harvested, or will be considered for harvesting under additional policies and selection criteria that may be further employed.

Figure 6:
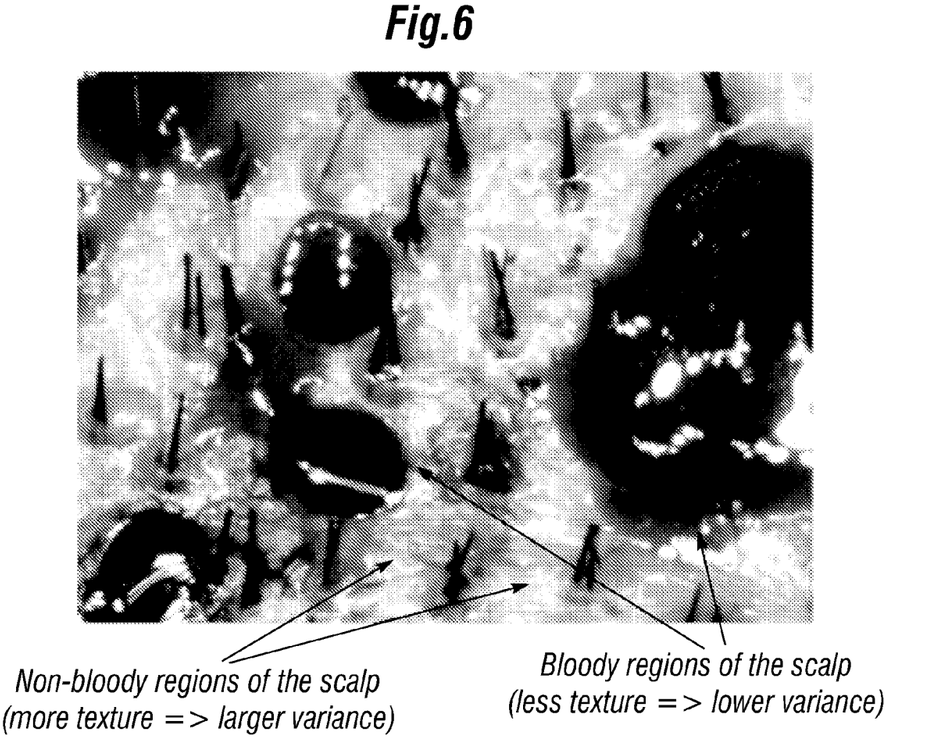
FIG. 6 is a print of the digital image demonstrating exemplary filtering of the candidate follicular units through blood detection using a variance filter.

One exemplary mechanism by which one can measure where in the "white flash" image the blood is prevalent is via a variance filter. FIG. 6 shows such exemplary blood detection using a variance filter. As could be seen from FIG. 6, bloody regions are characterized by little to no texture (low image variance) while non-bloodied regions of the imaged portion of the body surface, such as scalp, contain comparatively greater amounts of texture (high variance). Also, because there is some delay between the "white flash" and the normal red-field image (that may be on the order of, for example, two thirds of a second), the patient may move during even that brief time. Therefore, to increase the accuracy of the measurement, it is recommended to register the white flash image against the red-field image.

Figure 7:
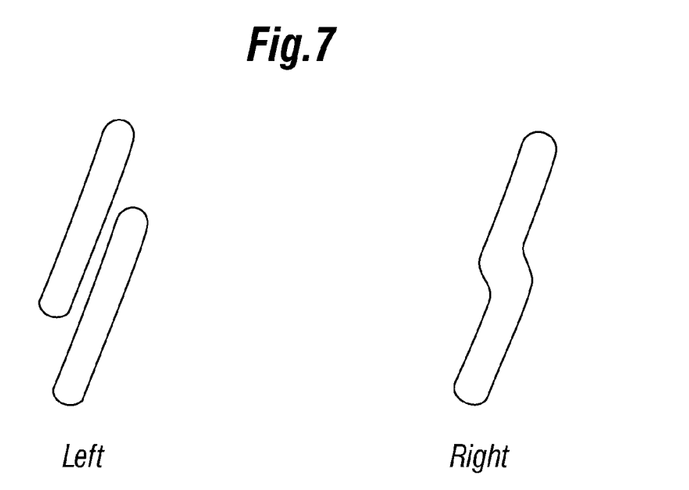
FIG. 7 is a schematic representation of another exemplary filtering criterion according to the method of the present invention.

FIG. 7 illustrates additional filtering criterion that could be used in a selection methodology according to the present invention. Sometimes, images of the objects in two different views (for example, from left and right cameras where stereo cameras are used) do not appear the same. One example of such situation is shown in FIG. 7 where two separate FUs can be easily identified in one image of the stereo pair (in this case the left image), while in the corresponding other stereo image the two segmented FU images have morphed into a single object. This scenario is typically encountered in high-density areas of the scalp where the hairs might be longer than 2-3 µm, and the combination of the tool vantage point (and by extension the camera axis) and imaging noise prevent the FUs from being imaged as completely separate in both left and right stereo views. While generally more advanced imaging systems are capable of "virtually splitting" the FUs where they have morphed together; the tracking of such hairs can be more burdensome and problematic due to the asymmetric views from the left and right cameras. As a result, to simplify and speed up the process of hair harvesting, one may choose to exclude these FUs all together and prefer to harvest the easier ones. As will be appreciated by those skilled in the art, many other filtering criteria may be implemented with the method of the present invention. These various criteria may be used individually or in numerous combinations depending on the specific needs and conditions in each harvesting case. As was previously mentioned, any of the filtering criteria may be turned "on" or "off" as desired.

Returning now back to FIG. 1, after the FU filters have been applied, there remains a set of filtered candidate FUs from which one can choose a certain number for harvesting. This selection block accomplishes this task by sorting the candidates based on one or more of the policies. There may be a variety of different policies chosen in the method of the present invention. In some situations only one policy (N=1) may be chosen, in other situations it could be a combination of a plurality of policies (N>1). As the policies could be turned "on" or "off," only active policies (those that are "on") will be followed. Below are listed some non-limiting examples of the useful policies.

To improve the speed and reduce the time of the procedure, one may choose a policy based strictly on the distance between the candidate FU and the position of the harvesting tool. In other words, the policy may be to pick the FU that is closest to the tip of the harvesting tool (which could be a needle, a cannula, a punch, and any other appropriate tool). Another alternative policy may be based on the amount of adjustment needed to align the tool with the FU so that the system will choose that FU whose orientation most closely matches the orientation of the FU that was just previously harvested. This way, the orientation of the tool does not need to be changed which will accelerate the entire process. The exemplary policies provided above are predicated solely on maximizing the throughput of the system, however, other considerations may govern the policy selection as well. For example, the policy may be based on improving the quality of the harvested hair, reducing transaction rates and similar considerations. One example of such policy is a selection of the FU whose emergence angle off the scalp or other relevant body surface is the greatest amongst a pool of candidates. The premise of this policy is that it is known that transection rates are lowest when the FU of interest points straight up with respect to the body surface rather than lying along the surface or having a very small emergence angle. The needle or other harvesting tool usually tends to skip and slide across the scalp when the FU in question lies flat, therefore, the above policy will increase the chances of correct alignment and operation of the tool in harvesting FUs with larger emergence angles.

In some embodiments of the present invention, one may choose a combination of any of the three exemplary policies mentioned above, or any other policies. This is achieved by assigning certain weight to each policy (a variable) and then scoring candidates FUs as a weighted sum of variables. Note that a particular policy may be assigned a zero weight in some instances so that it will not be included into consideration. If all three above-mentioned policies are taken into consideration, then in this example the score of each considered FU will be determined as follows:

FU score=(alpha)(distance to needle)+(beta)(delta from previous FU's orientation)+(gamma)(emergence angle)

wherein alpha, beta and gamma are "weight" assigned to each policy.

When automation is performed with a large number of FUs, multiple images of various locations on a body surface may be taken, including in multiple fields-of-view, so that a super-set of candidate FUs could be generated. This super-set is then used as an input "Candidate FUs" in block 100 of FIG. 1, and the subsequent process is similar to that described with reference to FIG. 1 as if only a single FOV was used.

According to another aspect of the present invention a method of selecting an order of harvesting of follicular units is based on another policy that is designed to plan ahead for any potential future hair harvesting procedures that may be required for the same patient. It has been determined that certain individuals may require several hair transplantation procedures over the course of their lives. In some situations, they may need additional procedures because they will continue to lose hair and may need a repeat after a certain number of years. In some cases, the multiple procedures spread over a certain period of time are planned ahead of time by physicians and patients. In contemplation of the future procedures where additional hair may need to be harvested from the same general area, for better aesthetic results one may want to space out follicular units that will be harvested during the first procedure. That way, when more hair will be later harvested during the subsequent procedure, the donor area will still look full, even and natural. The premise behind this policy is to take into account the desired yield for the current procedure, while also remaining cognizant of any future procedures.

Figure 8A:
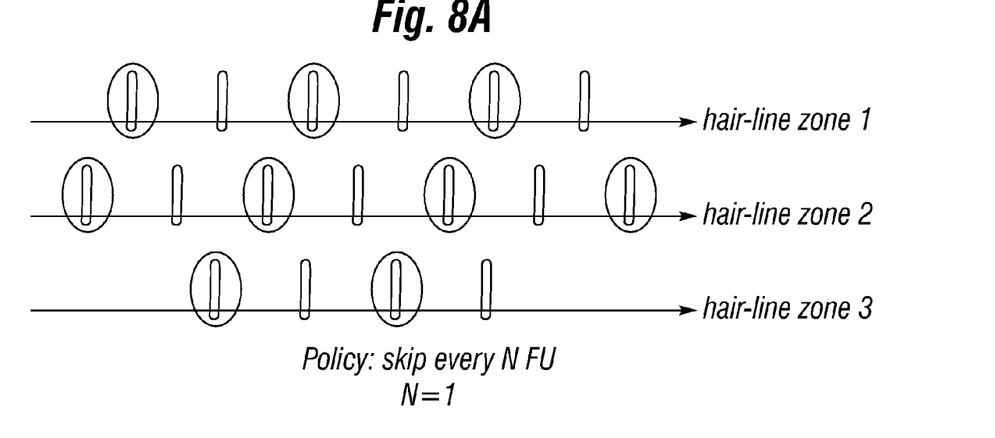
FIG. 8A is a schematic representation of an exemplary selection policy according to the present invention.

With reference to FIGS. 5A-C, it is described now an exemplary method of the present invention based on multiple procedure planning policy. For example, to address the issue described above, one exemplary policy is to skip every $N^{th}$ follicular unit in a given pool of candidate follicular units. FIG. 8A shows the "skip policy" on a donor area, such as a scalp, where N=1. In other words, every other follicular unit is chosen for harvesting. The circled FUs represent selection of every other FU in a given hair-line zone. In the example of FIG. 8A, it is linear hair-line zones 1, 2 and 3. As could be seen from FIG. 8A, the total number of harvested FUs is 9. In this example, after the first procedure is completed, every other FU in the selected hair-line zones will be harvested. Such policy will work if no significant additional harvesting is anticipated in the same hair-line zones.

Figure 8B:
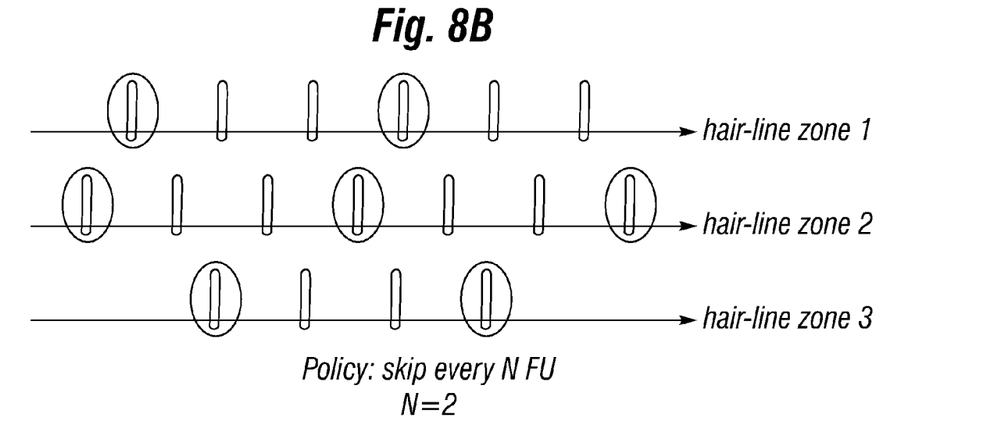
FIGS. 8B-C are schematic representations of alternative exemplary selection policies according to the present invention
Figure 8C:
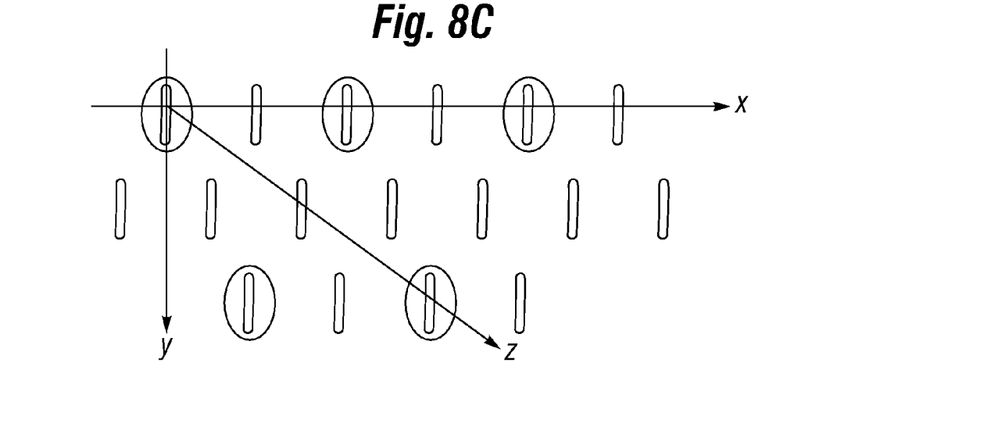

If it is necessary to remove more hair from the same zone or area in the future, it will be advisable to skip a plurality of FUs between each harvested FU in order to prevent large gaps between the remaining FUs. FIG. 8B shows a policy where a physician has taken into account future procedures in the same donor area and instead selected to dial N=2 into this policy. As a result, every two FUs were skipped so that the total number of FUs chosen for harvesting is now 7 instead of 9 of FIG. 8A. In the examples of FIGS. 5A-B the spatial grouping of FUs was performed in a linear fashion and in the same direction for hair-line zones 1, 2 and 3, however, the present invention is not limited to such linear unidirectional selection. For example, a skipping pattern for follicular units may be chosen from one or more various planning templates. Some exemplary skipping patterns may include one or both unidirectional and linear template of selecting every $N^{th}$ follicle in a hair-line. However, there is nothing preventing the applicability of this policy using multidirectional and non-linear selections, including other groupings, for examples patches or clusters, as shown by example in FIG. 8C along 3 exemplary directions x, y and z. 15.

Figure 9:
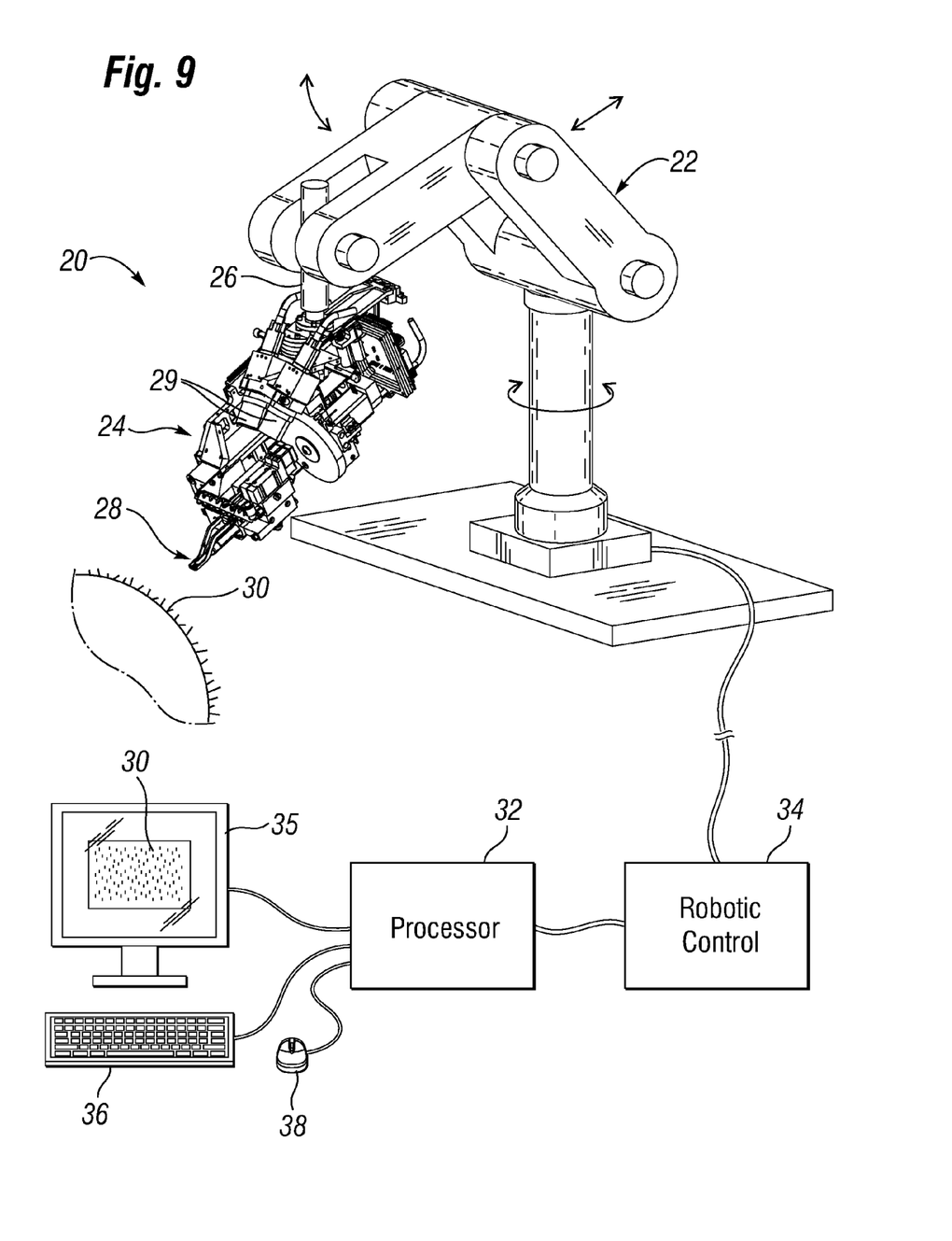
FIG. 9 is a depiction of an exemplary embodiment of the present invention implemented in a robotic hair harvesting procedure.

Any of the systems and methods for selecting follicular units for harvesting, as described herein, may be used in conjunction with the robotic systems for hair harvesting and transplanting similar to those described in the Bodduluri et al. publication. For instance, the system described in the Bodduluri et al. publication may be programmed and configured to perform the methods of selecting a follicular unit according to the present invention. FIG. 9 is a schematic perspective view of one such exemplary robotic system 20 for hair harvesting (and, optionally, implanting). The system 20 includes a robotic arm 22 and an assembly 24 mounted, for example, for rotation on a down tube 26 of the robotic arm. Various arrows are shown to illustrate the movement capabilities of the system 20. Various motors and other movement devices may be incorporated in the assembly 24 to enable fine movements of an operating tip of a tool 28 in multiple directions. The exemplary robotic system 20 further includes at least one imaging acquisition device 29, which is described in more detail below. The image acquisition device may be mounted in a fixed position, or it may be coupled (directly or indirectly) to a robotic arm or other controllable motion device. The operating tip of the tool 28 is shown positioned over a body surface 30, in this case a part of the patient scalp having hair follicles thereon. The tool 28 is any number of harvesting tools useful for removing follicular units from the body surface 30.

A processor 32 of FIG. 9, comprises an image processor for processing images obtained from the image acquisition device 29. The processor 32 may also instruct the various movement devices of the robotic arm 22 and the assembly 24, including the harvesting tool, and act, for example, through a robotic control 34 as schematically shown in FIG. 9. The robotic control 34 may be operatively coupled to the robotic arm and configured to control the motion of the robotic arm, including the motion based on the images or data acquired by the image acquisition device. Alternatively, robotic control 34 may be incorporated as a part of the processor 32, so that all processing and controls of all movements of all the tools, including harvesting tools, the robotic arm and any other moveable parts of the assembly, including those based on the images or data acquired by the image acquisition device, are concentrated in one place. The system 20 may further comprise a monitor 35, keyboard 36, and mouse 38. A magnified image of the body surface 30 can be seen on the monitor 35. In addition, the system may comprise other tools, devices and components useful in harvesting, and/or implantation of the FU, or in hair treatment planning.

Some non-limiting examples of an image acquisition device 29 shown in FIG. 9 include one or more cameras, such as any commercially available cameras. The image acquisition device may take still images, or it could be a video recording device (such as a camcorder) or any other image acquisition device. While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system, shown incorporated in the processor 32 in FIG. 9, to control the imaging operation and process image data. The image processor for use in the present invention may comprise any suitable device programmed and configured to perform the method of selecting FU for harvesting according to the present invention. In one exemplary embodiment, the image processor for selecting FU is configured for identifying a pool of candidate follicular units for harvesting in one or more images obtained from an image acquisition device; automatically sorting FUs in the pool of candidate follicular units based on one or more policies (such as those designed to improve speed, quality, or efficacy of the hair harvesting); and automatically selecting a particular follicular unit to be harvested next, wherein a selected follicular unit is one of the best available follicular units based on the at least one or more policies.

By way of example, and not limitation, a suitable image processor may be a digital processing system which includes one or more processors or other type of device. For example, an image processor may be a controller or any type of personal computer ("PC"). Alternatively, the image processor may comprise an Application Specific Integrated Circuit (ASIC) or Field Programmable Gate Array (FPGA). The image processor may also include memory, storage devices, and other components generally known in the art and, therefore, they do not need to be described in detail here.

The image processor for selecting follicular units could be used in conjunction with various manual, partially automated and fully automated (including robotic) hair transplantation and treatment systems and devices, including but not limited to systems for hair harvesting, or hair transplantation. Similarly, the image processor of the present invention could be used with hair classification systems, or with hair treatment planning systems.

Figure 10:
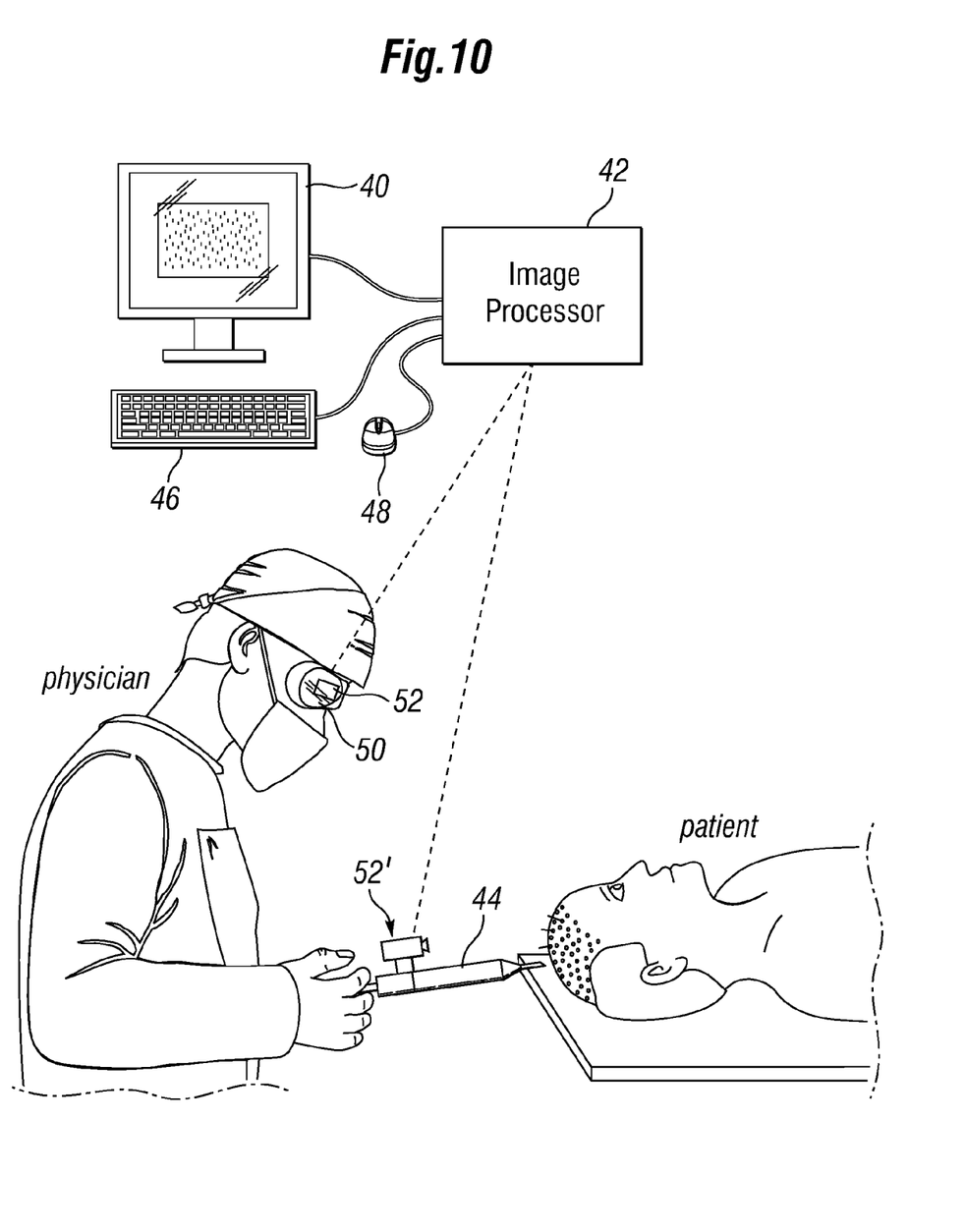
FIG. 10 is a depiction of an exemplary embodiment of the present invention implemented in a non-robotic hair harvesting procedure.

According to another aspect of the present invention, automatic follicular unit selection may be also implemented in a procedure conducted by the doctor using some hand-held tool for hair harvesting. One such exemplary implementation is shown as an example in FIG. 10. In this embodiment, a physician is conducting a manual operation on the patient using a hand-held harvesting tool 44 and wearing the typical glasses 50 that have high-magnification lupes. An image acquisition device 52, such as one or more cameras, may be attached to the glasses. The camera(s) may have viewfinders such that when attached to the glasses it allows the physician to view exactly what the cameras are imaging. Alternatively, the cameras 52' may be attached to the hand-held instrument or tool that physician is using for hair harvesting. In some additional embodiments, it may be a stand-alone image acquisition device. FIG. 10 shows two of the alternative examples of the image acquisition device as 52 (on the glasses) and 52' on the tool 44. The image processor, such as the computer 42, may execute the selection method of the present invention and perform the scene analysis, including highlighting of the follicular units based on the specified policies and/or filters. The monitor 40 displays the highlighted follicular unit or units, as well as other useful data/statistics, for example, an exact count of hair, approximate density, follicular unit types, etc. Guided by the information displayed on the monitor, physician may select the next follicular unit for harvesting.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention. For example, an article of manufacture of the present invention may comprise a machine-accessible medium including data that, when accessed by a machine, cause the machine to perform operations, such as identifying a pool of candidate follicular units for harvesting in one or more images obtained from an image acquisition device; automatically sorting follicular units in the pool of candidate follicular units based on one or more policies designed to improve one or more of speed, quality and efficacy of the hair harvesting; and automatically selecting a particular follicular unit to be harvested next, wherein a selected follicular unit is one of the best available follicular units based on the at least one or more policies.

A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage, flash memory device, optical storage, random access memory, etc.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Similarly, the invention is not limited to the use of a robotic system including a robotic arm, and that other automated and semi-automated systems may be utilized. Moreover, the system and method for selecting follicular units for harvesting of the present invention can be a separate system used along with a separate automated transplantation system or even with a manual transplantation procedure.

What is claimed is:

1. A method of selecting an order of harvesting follicular units, comprising:
    using a processor to:
    automatically sort a pool of candidate follicular units based on one or more policy; and
    automatically select among those automatically sorted a particular follicular unit to be harvested next, wherein the particular follicular unit is selected according to one or more additional policy,
    wherein the one or more policy, or the one of more additional policy is based on at least one of 1) appearance of follicular units in one or more images of a body surface in a predetermined preceding time interval, 2) location of follicular units within a certain distance to an item comprising one or more of another follicular unit, an edge of the field of view of the image, or a previous harvesting location, 3) follicular unit type, 4) follicular unit distance to a harvesting tool, 5) follicular unit orientation relative to an orientation of the harvesting tool, 6) follicular unit emergence angle from a body surface, wherein those follicular units that have less than a predetermined emergence angle from the body surface are rejected, or 7) a shape of follicular unit.

2. The method of claim 1, wherein automatically selecting the particular follicular unit is based on a combination of a plurality of filters and policies.

3. The method of claim 1, further comprising identifying the pool of candidate follicular units for harvesting in the one or more images of the body surface containing follicular units; and wherein automatically sorting comprises keeping only those follicular units that have consistently appeared in the one or more images in the predetermined preceding time interval.

4. The method of claim 1, further comprising harvesting the selected follicular unit.

5. The method of claim 1, wherein the steps of automatically sorting and selecting are continuously repeated.

6. The method of claim 1, wherein the one or more policy, or the one or more additional policy comprises 1) discarding follicular units that are located within a certain minimum distance to a location containing blood; or 2) keeping follicular units that are located outside a certain minimum distance to a location containing blood.

7. The method of claim 1, wherein the location containing blood is determined using a variance filter.

8. The method of claim 1, wherein the one or more policy, or one or more additional policy comprises 1) discarding follicular units that are less than a predetermined width, or 2) keeping follicular units that are equal or more than a predetermined width.

9. The method of claim 1, wherein the one or more policy, or one or more additional policy comprises 1) discarding follicular units that do not meet a predetermined criteria based on a number of hairs in the follicular units; or 2)

keeping follicular units that meet a predetermined criteria based on a number of hairs in the follicular units.

10. The method of claim 1, wherein the one or more policy, or the one or more additional policy comprises discarding follicular units possessing a complex shape or keeping follicular units possessing a simple shape.

11. The method of claim 1, wherein automatically selecting follicular units comprises scoring follicular units based on a weighted sum of variables associated with the one or more additional policy.

12. The method of claim 1, wherein automatically sorting follicular units comprises skipping every Nth follicular unit in the pool of candidate follicular units.

13. The method of claim 11, wherein scoring of follicular units based on the weighted sum of variables occurs after discarding one or more follicular units from the pool of candidate follicular units.

14. The method of claim 1, further comprising maneuvering a robotic arm of a robotic system to place a hair harvesting tool operatively connected to the robotic arm next to the selected follicular unit to be harvested.

15. The method of claim 12, wherein the skipping pattern comprises a multidirectional template of selecting every $N^{th}$ follicle in a patch or cluster of follicular units.

16. A method of selecting an order of harvesting follicular units using a robotic hair transplantation system, comprising:
   automatically sorting a pool of candidate follicular units based on one or more policy;
   automatically selecting among those automatically sorted a particular follicular unit to be harvested next, wherein the particular follicular unit is selected according to one or more additional policy; and
   wherein automatically selecting comprises scoring follicular units based on a weighted sum of variables associated with two or more of 1) appearance of follicular units in one or more images of a body surface in a predetermined preceding time interval, 2) location of follicular units within a certain distance to an item comprising one or more of another follicular unit, an edge of the field of view of the image, or a previous harvesting location, 3) follicular unit type, 4) follicular unit distance to a harvesting tool, 5) follicular unit orientation relative to an orientation of the harvesting tool, 6) follicular unit emergence angle from a body surface, or 7) a shape of follicular unit.

17. The method of claim 16, further comprising automatically filtering follicular units from the pool of candidate follicular units based on a predetermined criterion.

18. The method of claim 17, wherein a combination of the filtering criterion and one or more policy, or additional policy, comprises proximity to blood on a surface, a preference of the follicular units comprising one or more of follicular units located within a minimum distance to a hair harvesting tool, and follicular units whose orientation matches the orientation of a follicular unit that has been harvested immediately prior to the current selection.

19. A system for selecting follicular units for harvesting, comprising:
   an image processor, the image processor comprising instructions for:
      identifying a pool of candidate follicular units for harvesting in one or more images obtained from an image acquisition device;
      sorting follicular units in the pool of candidate follicular units based on one or more policies; and
      selecting a particular follicular unit to be harvested next, wherein the particular follicular unit is selected according to one or more additional policy,
   wherein the one or more policy, or the one of more additional policy is based on at least one of 1) appearance of follicular units in one or more images of a body surface in a predetermined preceding time interval, 2) location of follicular units within a certain distance to an item comprising one or more of another follicular unit, an edge of the field of view of the image, or a previous harvesting location, 3) follicular unit type, 4) follicular unit distance to a harvesting tool, 5) follicular unit orientation relative to an orientation of the harvesting tool, 6) follicular unit emergence angle from a body surface, wherein those follicular units that have less than a predetermined emergence angle from the body surface are rejected, or 7) a shape of follicular unit.

20. The system of claim 19, wherein automatically selecting follicular units comprises scoring follicular units based on a weighted sum of variables comprising one or more of follicular unit type, follicular unit distance to a harvesting tool, follicular unit orientation relative to an orientation of a harvesting tool, or follicular unit emergence angle from a body surface.

21. The system of claim 19, further comprising a memory operatively associated with the processor.

22. The system of claim 19, further comprising an image acquisition device wherein the image acquisition device comprises at least one camera.

23. The system of claim 19, wherein the image processor is a personal computer.

24. The system of claim 19, wherein the system is a robotic system and it further comprises a robotic arm.

25. A method of selecting an order of harvesting follicular units, comprising:
   using a processor to:
   identify a pool of candidate follicular units for harvesting in one or more images of a body surface containing follicular units;
   automatically sort the pool of candidate follicular units based on one or more policy;
   automatically select among those automatically sorted a particular follicular unit to be harvested next, wherein the particular follicular unit is selected according to one or more additional policy; and
   wherein the one or more policy or the one or more additional policy comprises keeping only those follicular units that have consistently appeared in the one or more images in a predetermined preceding time interval or rejecting those follicular units that have not consistently appeared in the one or more images in the predetermined preceding time interval.

* * * * *